(12) United States Patent
Buckingham et al.

(10) Patent No.: US 7,171,279 B2
(45) Date of Patent: Jan. 30, 2007

(54) ARTICULATING ARM FOR POSITIONING A TOOL AT A LOCATION

(75) Inventors: Robert Oliver Buckingham, Bristol (GB); Andrew Crispin Graham, Bristol (GB)

(73) Assignee: Oliver Crispin Robotics Limited (GB)

( * ) Notice: Subject to any disclaimer, the term of this patent is extended or adjusted under 35 U.S.C. 154(b) by 40 days.

(21) Appl. No.: 10/370,190

(22) Filed: Feb. 19, 2003

(65) Prior Publication Data

US 2003/0229420 A1 Dec. 11, 2003

Related U.S. Application Data

(63) Continuation of application No. PCT/GB01/03719, filed on Aug. 17, 2001.

(30) Foreign Application Priority Data

Aug. 18, 2000 (GB) ................................ 0020461.0

(51) Int. Cl.
G05F 19/04 (2006.01)

(52) U.S. Cl. .................... 700/50; 700/248; 318/568.12; 318/568.16

(58) Field of Classification Search ................ 700/245, 700/254, 260–262, 247, 248; 362/259, 423–424; 414/696, 751.1; 219/121.78; 901/14–16, 901/42; 74/490.02, 490.03; 701/25; 180/8.6; 318/568.12, 568.16

See application file for complete search history.

(56) References Cited

U.S. PATENT DOCUMENTS

| | | | |
|---|---|---|---|
| 4,347,837 A | | 9/1982 | Hosono |
| 4,641,251 A | * | 2/1987 | Inoue ........................... 700/52 |
| 4,703,157 A | * | 10/1987 | Dahlquist .............. 219/121.78 |
| 4,830,569 A | * | 5/1989 | Jannborg ..................... 414/729 |

(Continued)

FOREIGN PATENT DOCUMENTS

DE 35 34 479 A1 7/1986

(Continued)

OTHER PUBLICATIONS

Poi et al., Traveling wave locomotion hyper-redundant mobile robot, 1998, IEEE, p. 418-423.*

(Continued)

*Primary Examiner*—Thomas Black
*Assistant Examiner*—McDieunel Marc
(74) *Attorney, Agent, or Firm*—St. Onge Steward Johnston & Reens LLC

(57) ABSTRACT

A robotic arm device capable of accessing machinery and equipment, which is otherwise difficult access for maintenance and repair is provided. An apparatus comprising a support arm with a plurality of longitudinal segments each capable of movement one with respect to the other to define a serpentine path or shape, work head carrier located at or near the distal end of the arm and adapted to carry a work and or examination tool and controller for controlling the movement of at least some of the segments such that the arm may be advanced longitudinally along an access path to present the tool at the work location. The arm is formed by a combination of segments, each comprising a plurality of links with and may include a separate controller for each segment.

27 Claims, 6 Drawing Sheets

U.S. PATENT DOCUMENTS

| | | | | |
|---|---|---|---|---|
| 5,355,743 | A | * | 10/1994 | Tesar ........................ 74/490.03 |
| 5,564,312 | A | * | 10/1996 | Brunman et al. ......... 74/490.02 |
| 5,901,613 | A | * | 5/1999 | Forslund .................. 74/490.03 |
| 6,408,710 | B1 | * | 6/2002 | Kullborg et al. .......... 74/490.03 |
| 6,512,345 | B2 | * | 1/2003 | Borenstein et al. ..... 318/568.12 |
| 6,540,471 | B1 | * | 4/2003 | Brog.ang.rdh ............... 414/729 |
| 6,577,093 | B1 | * | 6/2003 | Hvittfeldt et al. ....... 318/568.11 |
| 6,636,781 | B1 | * | 10/2003 | Shen et al. .................. 700/248 |
| 6,675,069 | B2 | * | 1/2004 | Uratani ....................... 700/245 |
| 6,684,129 | B2 | * | 1/2004 | Salisbury et al. ........... 700/245 |
| 6,697,710 | B2 | * | 2/2004 | Wilcox ....................... 700/245 |
| 6,774,597 | B1 | * | 8/2004 | Borenstein ............. 318/568.12 |
| 6,870,343 | B2 | * | 3/2005 | Borenstein et al. .... 318/568.16 |

FOREIGN PATENT DOCUMENTS

| | | |
|---|---|---|
| DE | 34 04 824 A1 | 8/1986 |
| DE | 100 23 292 A1 | 2/2001 |

OTHER PUBLICATIONS

Killfoile, Snake robot, 2004, Internet, p. 1-9.*

* cited by examiner

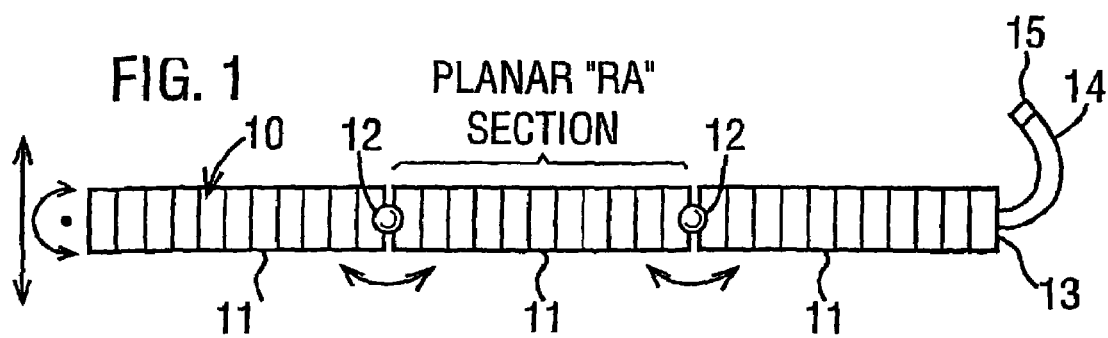
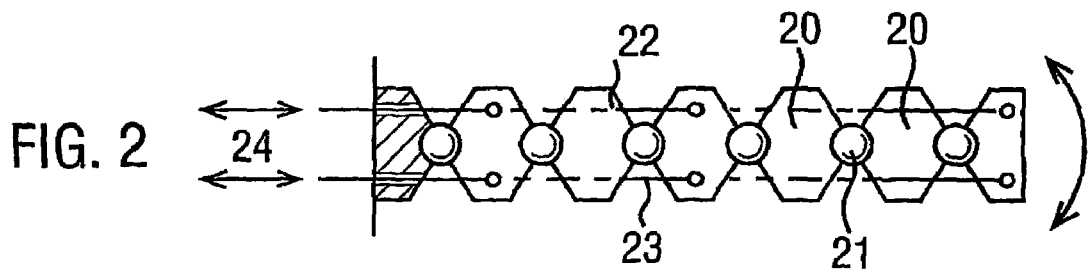
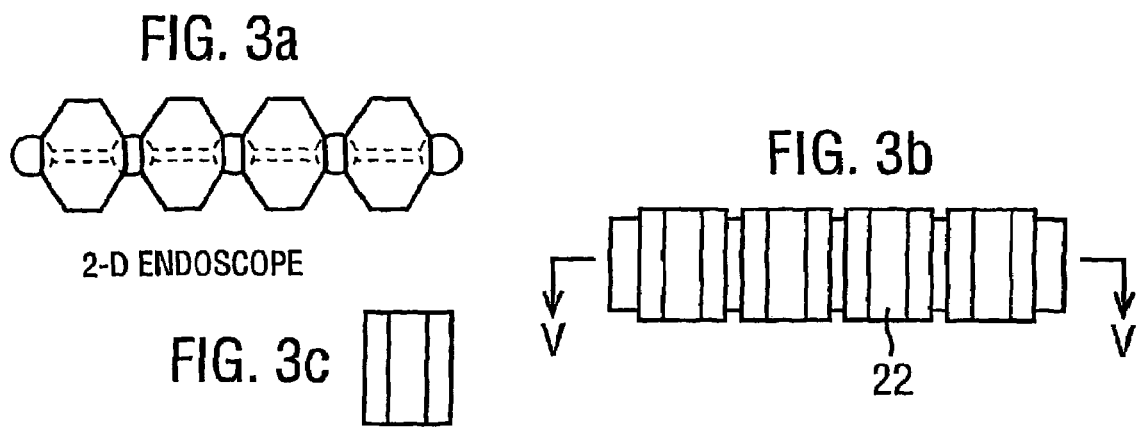
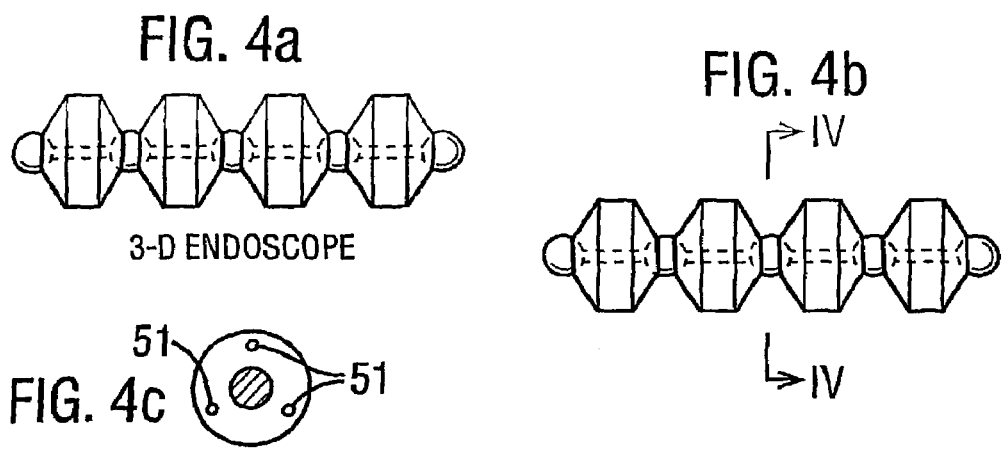

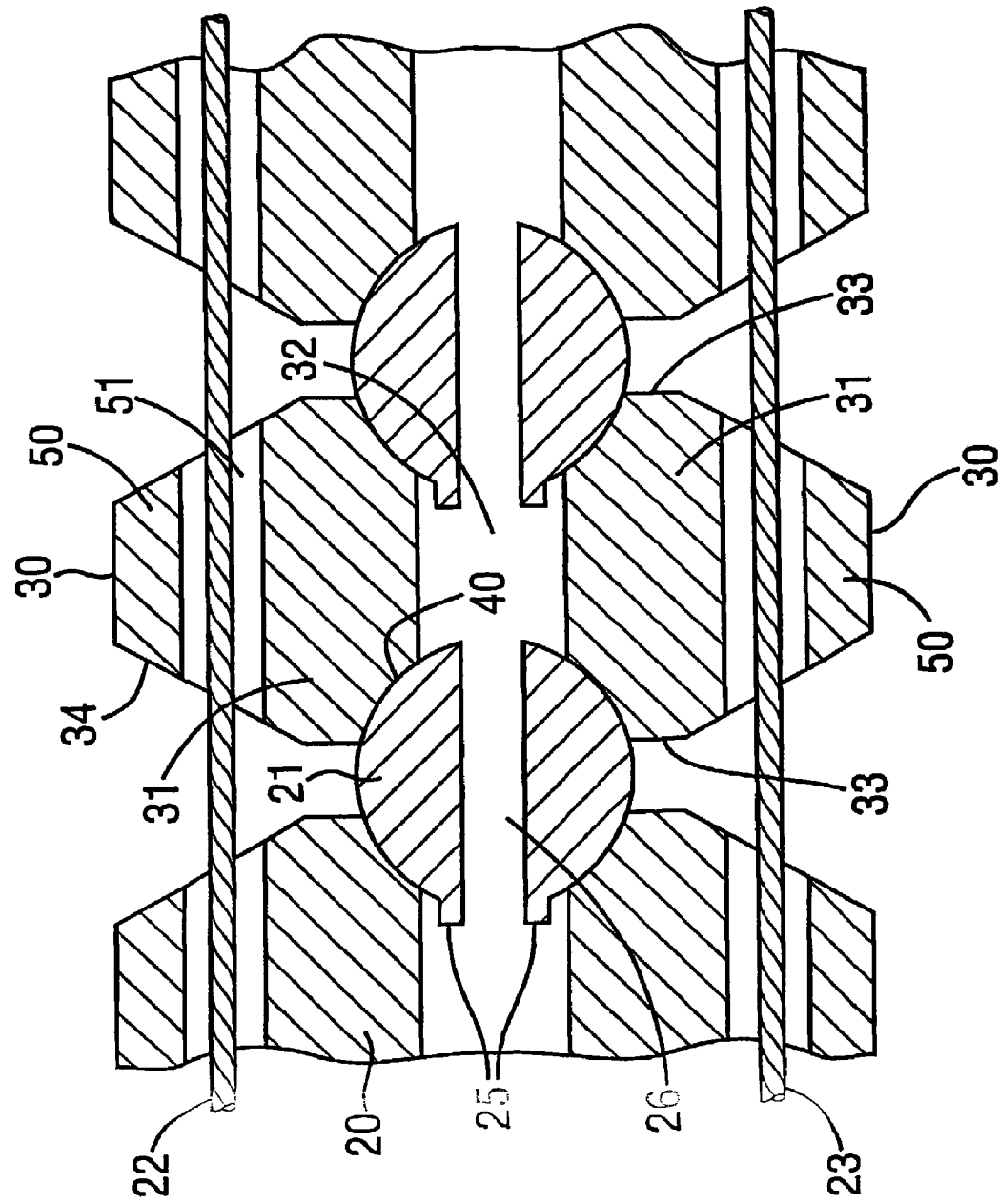

ARTICULATING ARM FOR POSITIONING A TOOL AT A LOCATION

CROSS-REFERENCE

This application is a continuation of pending International Patent Application No. PCT/GB01/03719 filed Aug. 17, 2001, which designates the United States and claims priority of pending British Application No. 0020461, filed Aug. 18, 2000.

FIELD OF THE INVENTION

The present invention relates to an improvement in the robotic positioning of work tools and sensors and relates in particular to improved mechanical and software tools for positioning a work tool or sensor and to control algorithms for effecting control of such equipment.

BACKGROUND OF THE INVENTION

Traditionally, mechanical equipment such as engines and machines encased by a housing have been maintained by regular maintenance schedules. In the event of a malfunction, an operative or engineer will run the machine or engine through a series of test functions in a trouble-shooting programme and note the reaction of the machine or engine to each test function. From observation of the action or reaction of the machine or engine to a given function, it is possible to diagnose, at least in part, the general area of malfunction of the machine. Thereafter the machine is dismantled to an extent sufficient to examine the possible malfunction and to repair the fault.

Such activity is time-consuming and on many occasions the trouble-shooting programme or the number of available diagnostic functions for the machine is insufficient to pinpoint with accuracy the precise location of the fault. On many occasions a machine or engine will need to be partially dismantled involving much wasted effort, particularly when the trouble-shooting regime or programme gives an false indication of a fault.

Hitherto, detailed inspection of machines or engines has involved the determination of changes in sound, the use of ultrasound examinations for cracks and breaks in equipment and also for x-ray analysis of particular components. In each case, however, these techniques only serve to assist in diagnosis of faults. Where the components concerned are readily accessible or where the machine has been partially dismantled, only then can examination of individual suspect components be undertaken.

In complex machines such as steam or gas turbine engines and the like, there is a need to determine faults in machine and to locate, with precision, the area of the fault before commencing stripping of the engine to examine the faulty component(s) closely for repair/replacement.

In medical science, it has, for many years, been the practice to use endoscopes to examine body cavities sometimes at quite significant distances from the point of access. An endoscope may typically have an examination light source and an optical receiving device at the distal end of a flexible support arm. It is entered into a body orifice and entry is continued until examination of the desired area of disease/damage is reached for internal examination. The flexible support arm is capable of adopting a serpentine path to follow the path of the body orifice. Thus, the walls of the body orifice serve to guide the endoscope and assist the endoscope in following its serpentine path. The use of endoscopes for the examination of machines and engines has been used with some degree of success. A major difficulty of such devices, however, is the problem of controlling the endoscope within the machine and arranging for the light and optical sensor to be disposed in the correct area of the machine for examination. Where the point of examination of the machine is near an access port then endoscopes have been fairly successful in the internal examination of complex machinery. Likewise, where the repair is similarly located near an access port and is a simple repair, for example, such as tightening a screw or grinding a metal surface then a working device such a borescope may be used.

A typical prior art proposal is set out in British Patent Specification No 2033973 which relates to a method of inspecting a gas turbine engine, which latter has a casing provided with at least one access aperture to allow inspection of engine components located within the casing the method comprising inserting guide means into the access aperture locating one end of the guide means being external of the casing and the other end of the guide means being located adjacent the engine component to be inspected fixing the guide means in said location and inserting a flexible endoscope or other remote viewing inspection apparatus into the guide means. In this case the guide means serves as the guide for the flexible endoscope rather in the manner of the body orifice described above.

In European Patent Specification No 0907077 there is described and claimed a method and apparatus for inspecting in situ a turbine engine blade in a stage of a gas turbine engine by using eddy currents, which examination is effected from a remote location. The engine includes a casing about the stage of the engine to be examined and a borescope hole which extends through the casing and into the stage in which the turbine blade in question is located. The turbine blade may be inspected by inserting the apparatus through the borescope hole in the turbine casing. In this case the essence of the invention is the use of the sensor probe means for holding eddy current coils and for sensing imperfections in the structure detected by induced eddy currents within the component, such as a turbine blade, being examined.

U.S. Pat. No. 5,644,394 relates to a system for repairing damaged airfoils for gas turbine engines including a plurality of rigid attachment tools. Each attachment tool is individually shaped to access a leading edge of a damaged airfoil of a particular stage of a gas turbine engine. The attachment tools enable repair of damaged airfoils without dissembling the gas turbine engine. In this case, however, the tools are rigid and are designed to operate juxtaposed the borescope opening into the engine housing.

British Patent Specification No 2154335 relates to a technoscope for internal inspection of a power plant such as an aircraft power unit equipped with noncircular preferably cornered, e.g. square, wall ports comprising a first rigid guide shaft of non-circular cross-section insertible into one of the wall ports and having a lateral distal outlet and a guiding element which passes through said first guide shaft and has a flexible distal portion an intermediate portion of its cross section matches that of the first guide shaft and a proximal control system for control deflection of said flexible distal end the guiding element is used to guide a flexible endoscope shaft to the desired site within the plant to be inspected. Again, a rigid guide shaft is used for insertion into a wall port and serves to provide support for a flexible guiding element which passes through said guide shaft as a sliding fit.

U.S. Pat. No. 5,803,680 also relates to an instrument such a technoscope for machining the surfaces of engine blades in normally inaccessible cavities having a machining tool able to be simultaneously observed at a machining location with an optic comprising an instrument shank to which the head is distally coupled, said head carrying the tool and being pivotable relative to the longitudinal axis of the instrument shank. In order to create the possibility of being able to measure damage to the surface to be machined with this instrument, a measuring tool with a measuring template is attached to the instrument head and when this instrument head is pivotable into the field of view of the optic the measuring tool may be attached to the head of instrument in a simple manner instead of a machine tool.

From the foregoing, therefore, it will be appreciated by a person skilled in the art, that there is a need for an internal examination and repair function without disassembling the machine or engine. It will be obvious to the person skilled in the art that maintenance carried out in this way has the considerable advantage of saving of time effort and cost by being able to effect a repair or an inspection without dismantling the engine or machine into its component parts.

The prior art, however, all suffers from the problem that in order to work on or examine a component or part, the area to be worked upon or the site to be observed, needs to be near the access port for the technoscope, borescope or endoscope as the case may be, or guide means must be provided to support the endoscope/borescope during its passage to the area of work/examination.

There is, therefore, a need for apparatus to inspect and/or work on a component of an engine which is more remote from the access port and where the access path is convoluted.

SUMMARY OF THE INVENTION

The present invention, therefore, seeks to overcome this problem of accessibility to remote parts of an engine by providing apparatus which is capable of following a convoluted path from an access port in an engine or machine to a work place or inspection site within the machine. The invention further seeks to provide apparatus which can be controlled by an appropriate algorithm for control of such equipment remotely whereby the work tool and/or optic may be guided to a work site by computer control of the support arm. The invention further provides apparatus on the form of an arm capable of extending longitudinally along a convolute path within the machine or engine from an access port to a work site.

The advantage of such apparatus is that it enables tools, inspection and test equipment to be carried deep inside an engine or machine to sites which would not normally be accessible without dismantling. A particular feature is that the invention does not need, although it may make use of, guidance or support intermediate the access port and the work/examination site. This permits for example, ultrasound examination of components such as, turbine blades to be carried out in situ with access to the leading or trailing edge and without the need to access the blade tip.

According to one aspect of the present invention, therefore, there is provided a method for inspecting or working on an engine or machine in which the work/inspection site is remote from an access point, which method comprises
 defining an access path within the engine or machine to said work/inspection site,
 mounting a work/examination tool at a distal end of a support arm having a plurality of articulated elements
 providing control means for at least some of said articulated elements, and causing or allowing said arm to enter said engine or machine and to advance longitudinally of itself to follow said access path to present the tool at the work/inspection site.

In another aspect of the present invention there is provided Apparatus for inspecting or working on an engine or machine by the method of the invention, which apparatus comprises
 a support arm comprising a plurality of longitudinal segments each capable of movement one with respect to the other to define a serpentine path or shape,
 work head carrying means at or towards the distal end of said arm and adapted to carry a work and or examination tool
 and control means for at least some of said segments to permit control of the shape of the associated segment so that different segments constituting the arm may assume different shapes whereby the arm may advance longitudinally along a predetermined access path to present said tool at said site.

In one particular aspect of the present invention the articulation between the segments in the arm are maintained under tension in order to provide rigidity of each articulation point. By maintaining the articulation of the links under tension in this way the spatial positioning of each articulation can be controlled precisely with time to enable the arm to follow a convoluted path to guide the work tool into the machine.

In a further aspect of the present invention each segment may be separately controlled. The separate control may comprise servo motor means. The servo motor means may be mounted on each segment or they can be remote from the segment with the segments themselves controlled or driven by wires. The motors may be hydraulic or pneumatic motors. The apparatus used in accordance with the present invention could be provided with a datum for a particular engine or machine and the algorithm for the control means may be provided to enable presentation of the work head to a particular position or location within the machine relative to that datum.

In a particular aspect of the present invention, each segment comprises a plurality of links, each link being capable of relative movement in at least two dimensions one with respect to another. The links may be a two-dimensional segment capable of operating in a single plane or may be a three-dimensional segment. Each link may be articulated with respect to its neighbour and the articulation means may comprise a roller in the case of the 2-D segment or ball in the case of the 3-D segment.

In a further aspect of the invention the articulation of the links in a segment may be maintained under tension by wires. This has the advantage of maintaining a stiffness of the joint and enables the segment to adopt a bent configuration with a degree of rigidity and control which would enable a force to be applied by the work head at the work site. Individual links in a segment may be "stiffened" to improve the load capacity and positional determinancy of each joint in the segment. This is important when determining the position of the arm in relation to its datum and for applications where a significant mass is to be supported at the end of the arm.

The stiffening may take the form of a spring or springs located in the gap between each link. The springs may be sized with two factors in mind; (1) the compressive force on the spring(s) will be slightly less than the total control wire tension, and (2) the "rocking" stiffness will be selected to give a specific bending stiffness to each joint.

The compressive force has the benefit of reducing the compression on the link ball joint, reducing the friction in the joint even with high wire tension. The bending stiffness introduces a tendency for the segment to conform to a curve of an arc (even with large loads carried by the arm), and reduces the negative effect of carrying services of unpredictable stiffness through the centre of the apparatus.

The stiffened device (stiffened by springs or by a flexible skin or housing or some other technique) is less affected by gravity, but the tension in the wires required to change the shape of the stiffened device is considerably higher. By varying the stiffness in combination with wire tension the device can be made to behave in different ways to produce the desired configuration.

The link disposition within a segment may be controlled by wires. At least two wires may be provided for each link whereby adjusting one wire with respect to another controls the attitude of one link member with respect to the next thereby causing or allowing the segment to "bend". The operating means may include drive means for operating through the length of the support arm and for operating a work piece attached to said work head. The control of the segment, the articulations between the links, and the spatial disposition may be controlled by computer means operating through one or more servo motors provided throughout the device.

In one embodiment of the present invention, each segment may comprise a plurality of links capable of allowing the segment to bend in two dimensions only. This enables the tension in of the control means to be flat ribbons or strips of material typically 25 micron or 50 microns spring steel strip. This approach enables banks of strips to be used in juxtaposition and simplifies the design features for each link since only one slot would be required for an entire ribbon stack for the control of a plurality of segments. In a typical embodiment, therefore, each link may comprise a guide path having arcuate edges or surfaces about which the strip(s) may bend while at the same time constrained in the extent of bending. Thus we have a single guiding element either side of an entire bundle of control ribbons that produces a simpler construction, which would, in the longer term, tend to be more reliable and cheaper.

It will be appreciated by the person skilled in the art that the contact pressure over a surface will be considerably lower than in the case of an equivalent wire. This allows improved lubrication with resultant frictional and wear reduction. Furthermore, in situations where access is required into a narrow but tall space, the design can be biassed towards such an arrangement. An additional advantage is that electrical conduit(s) may be included with the strip to provide additional control to actuators spaced lengthways along the arm. Thus, for example, it would be possible to provide a rotational joint between a pair of segments so that part of the arm may be oriented to bend at a plane different to the rest of the arm.

In a further embodiment of the invention, by providing the link axes offset from the centre line of the link in each case, or incline one slightly with respect to its adjacent neighbour, it is possible to create spiral behaviour to assist entering a convoluted space.

The control means may comprise redundant robot control means. In this connection, a robot is said to be redundant when a manipulator can reach a specified position with more than one configuration of the links.

The algorithm for control for said control means may comprise trajectory planning techniques and may further comprise a potential field algorithm which may typically be based on an adaptation of the Laplace equation.

The control means may be further adapted to move an arm to present a work head at a work site without contact with obstacles in the machine. In another aspect of the invention the control means may include an algorithm for taking into account moving obstacles within the machine during investigation and analysis.

In a typical aspect of the invention there is provided a multi-link planar redundant robot in which the links are servo controlled with set point data being provided from either real time or off-line calculation using a trajectory planning technique. In this way the robot may move to pre-determined goal points without hitting obstacles or by following the interstices between components within the machine or engine.

Apparatus in accordance with the present invention is capable of inspection and repair of turbine blades and other internal features of gas turbine and like engines while gaining access via the normal air path that is to say by gaining access to the internals of the engine are accessed through the interstices of the blades along the air flow path. The apparatus allows access to the internal features of an engine or machine along a non-straight path.

Apparatus in accordance with the present invention would be of interest in surgery for example in colonoscopy and ventriculoscopy.

Apparatus in accordance with the present invention could also be used in bomb disposal for cutting a hole in a bomb and then for access to the internals of the bomb to wash out and remove the explosives and/or to defuse the bomb.

The invention further envisages the use of multiple devices to do parallel inspections and work tasks simultaneously on an engine or machine and also conduct co-ordinated tasks such as grinding, waste removal and viewing.

In a further aspect of the present invention the support arm comprises a hyper redundant snake robot control path borescope which is made up of a plurality of segments. Between each segment, there is a joint and each segment is individually controlled with respect to the preceding segment. The segment length and the maximum angle between the segments is a function of design and may depend on the task for which the arm to be employed. The motion of the device may be controlled by computer so that the device can follow its nose along a specified path. These devices can operate in 2-D or 3D depending upon the task and can within reason have any length. The cross-section of the device can vary along its length and the device can also be hollow and have channels for tools and services and the like. In one aspect of the invention the control motors can be mounted in each segment or each motor can be connected remotely by wires.

The tools that may be carried by the work head include vision, ultrasound, or eddy currents sensors and these could be changeable. The work head may also incorporate expansion means for clamping the work head relative to fixed components in the machine thereby to provide a basis for operation of a tool in the work head relative to a datum provided by the positioning of the clamp.

In a particular embodiment of the invention the control means includes computer control means operational in response to an algorithm to operate in combination with a CAD model of the engine so that known positions of the access path can be calculated off-line. This will enable apparatus in accordance with the invention to be deployed to a given engine and for the arm to extend into the engine by a predetermined path in accordance with a pre-set algorithm for that particular engine based on CAD modelling. This enables more rapid deployment of the apparatus to its operational position.

The following is a description by way of example only and with reference to the accompanying informal drawings of methods of carrying the invention into effect.

BRIEF DESCRIPTION OF THE DRAWINGS

In the drawings:

FIG. 1 is a diagrammatic view of part of a multisegment arm in accordance with the present invention;

FIG. 2 is a diagrammatic view of part of a segment of FIG. 1 showing individual links;

FIG. 3a is a side view of a two-dimensional segment of FIG. 2;

FIG. 3b is a plan view of 3a;

FIG. 3c is a detail of 3b;

FIG. 4a is a side view of a three-dimensional segment of FIG. 2;

FIG. 4b is a plan view of FIG. 4a;

FIG. 4c is a cross-section on line iv—iv of FIG. 4b;

FIG. 5 is a longitudinal section along the line v—v of FIG. 3b;

FIG. 6b is an alternative embodiment to 6a;

FIG. 7b is a further embodiment of FIG. 7a.

DETAILED DESCRIPTION OF THE DRAWINGS

Figure 6A:
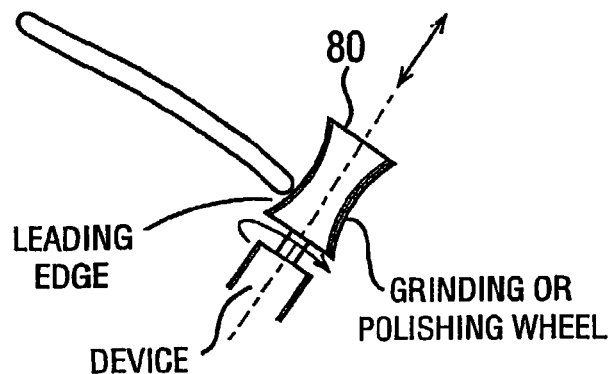
FIG. 6a is a diagrammatic representation of a work head in its operative position.

One aspect of the invention as illustrated in FIG. 1 comprises a longitudinally extending multi-segment arm part of which is indicated generally at 10. The arm comprises a plurality of individual links 11 each of which is articulated one to another by articulated joint 12. The distal end 13 of the arm carries a further segment 14 as hereinafter described terminating in a work head 15. Each segment 11 is a multi-link section (see FIG. 2) comprising a plurality of individual links 20 each interconnected by a connecting element 21 about which link 20 is capable of limiting arcuate movement. The arrangement is such that each link 20 alternates with an element 21 the arrangement being such that the links of a segment are capable of deflecting about an arc in at least one plane such is as illustrated in FIG. 3a, which illustrated a 2-D segment. FIG. 3b is an plan view of the 2-D segment per FIG. 3a, and FIG. 3c is a detail of an individual link as seen in plan view per FIG. 3b. Referring back to FIG. 2 and 3b, each link 20 is connected by means of control wires 22, 23 to control means 24 for applying tension to said wires. In the rest position with the segment extended as shown in FIG. 2, the wires are maintained under equal tension in a leftward direction (see FIG. 2). This maintains each of the elements 21 under a degree of kinetic stability. To enable bending, the individual wires to each link are subjected to increasing tension in one direction and a relaxation of tension in the other. Thus, as shown in FIG. 2 an increase in tension of the upper wires indicated generally at 22 and a corresponding relaxation of tension of the lower wires 23 would result in a flexing or bending of the segment arrangement in an upward direction.

In a two-dimensional segment, each of the elements 21 is generally cylindrical extending transversely of the axis of the segment, each element also having a central transverse diametric bore 26 substantially longitudinally of the segment 11. The element 21 is provided on one side with a lip 25 extending along a surface of the element and embracing bore 26. Each link 20 extends the width of the segment and is contoured in cross-section to provide, as shown in FIG. 5, a central body portion 31 provided with a central bore 32 and outer portions 50 defining an outer surface 30 and having inclined faces 34 to allow adjacent links to "bend" about an element 21 without interference between the surfaces of adjacent links. The central body portion of each link has a face 33 and is provided with a central transverse groove 40 which is adapted to accommodate the arcuate surface of cylindrical connecting element 21 the arrangement being such that the cylindrical connecting element 21 is disposed relative to its adjacent contiguous link 20 such that the central bore of element 21 is substantially coaxial with the bore of its adjacent links 20 when the links are maintained in a "straight" configuration. The longitudinal lip 25 on each element 21 serves to limit relative rotation between each link and its adjacent element.

Each of the outer portions 50 of each link is provided with a longitudinal through cavity 51 in substantially spaced parallel relationship with the axis of bore 32. Cavity 51 is intended to accommodate one or more control wires 22, 23 for the purpose of controlling the link array.

Figure 8:
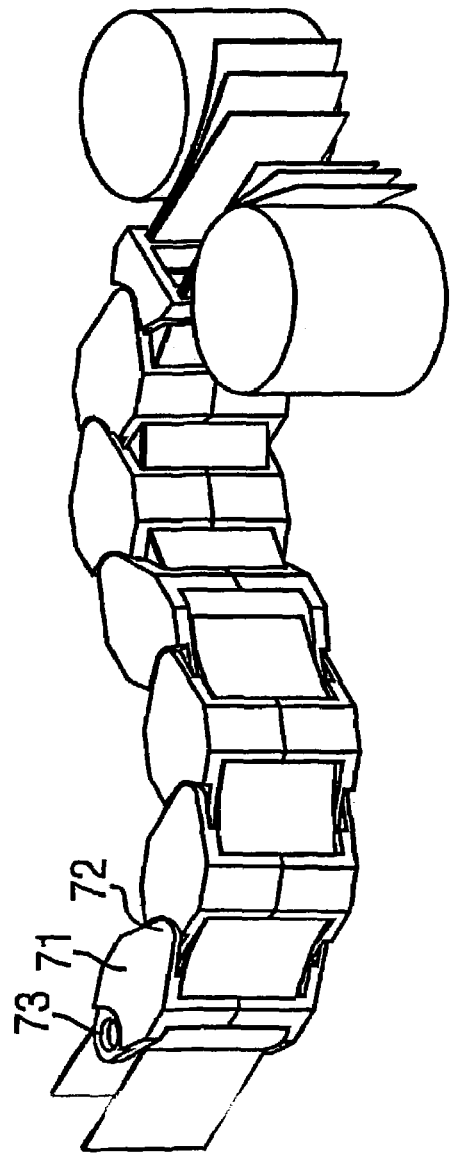
FIG. 8 is a perspective view of a 2-D arm in accordance with the present invention.
Figure 10:
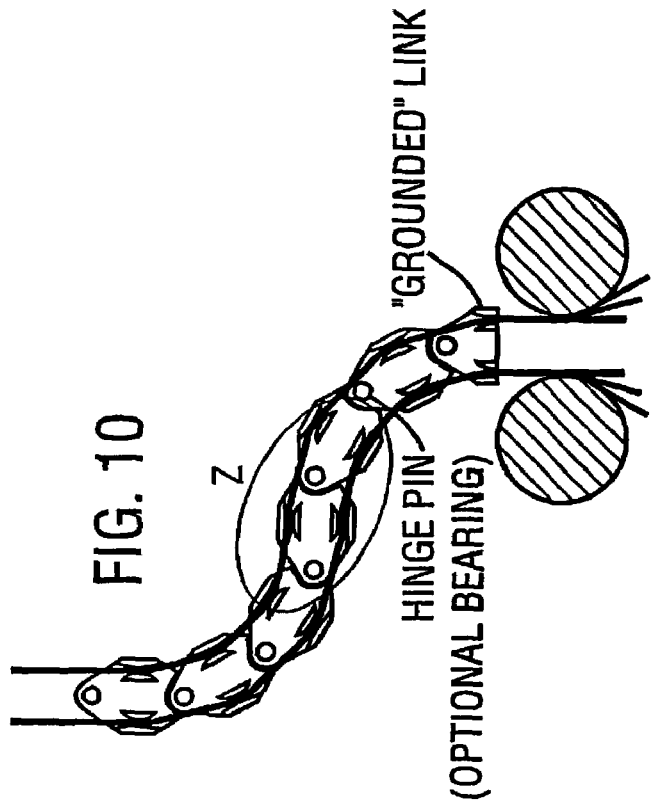
FIG. 10 a section through the device of FIG. 9
Figure 9:
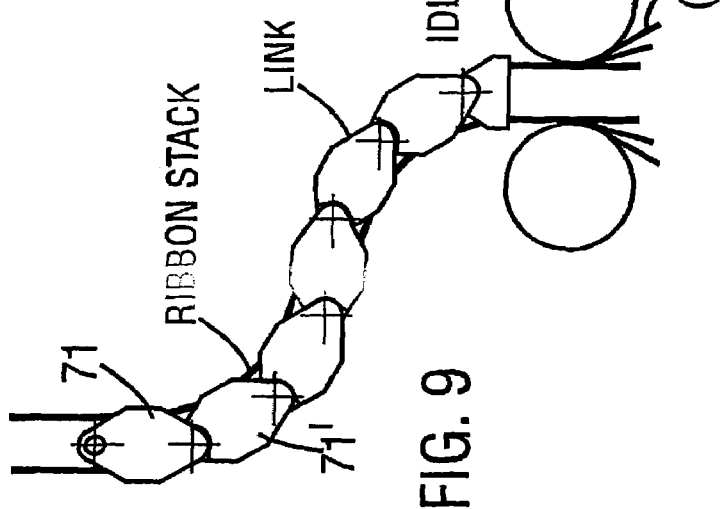
FIG. 9 is a top view of the device of FIG. 8.
Figure 11:
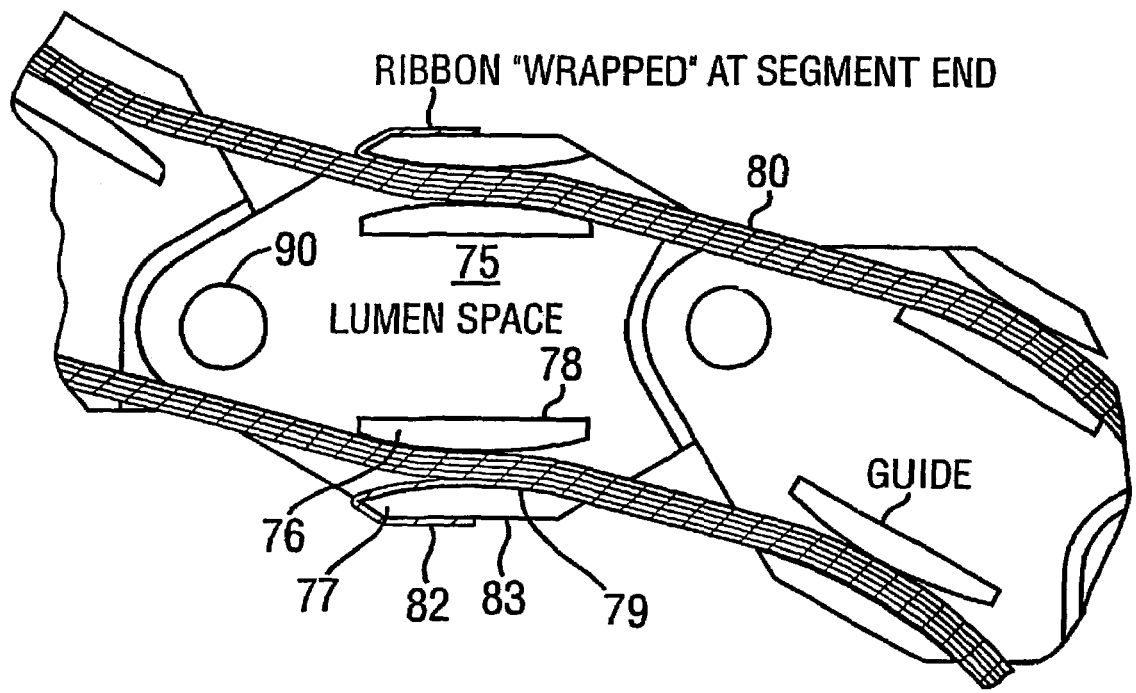
FIG. 11 is a detail of portion 'Z' in FIG. 10.
Figure 12:
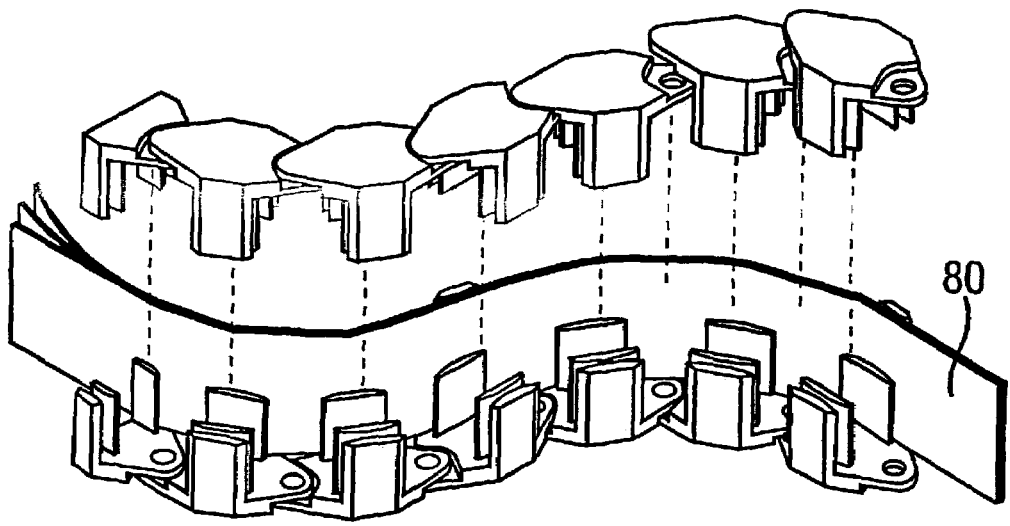
FIG. 12 is a diagram showing the installation of a control strip for ribbon in of the segment of FIG. 8

Another embodiment of a two-dimensional device in accordance with the present invention is illustrated in FIG. 8. In FIG. 8, each link 71 is substantially elongated and provided with a nose portion 72 at each end. One end of each link portion is recessed and 73 and is in adapted to receive the projecting nose portion 72 of an adjacent link the arrangement being such that adjacent links 71 and 71'—(see FIG. 9) are capable of limited pivotal movement one with respect to the other in a two-dimensional plane. Each link 71 is provided with a central body portion indicated generally and 75 see FIG. 11, which body portion carries a pair of upstanding guide members 76 and 77 respectively. Each of guide members 76 and 77 is provided with an arcuate in a surface 78, 79 for the purpose of engaging with a control ribbon passing thereover. As shown in FIG. 11, a plurality of control ribbon elements 80 are applied and passed through the spacing between guides 76 and 77 respectively as a stack of ribbons. Each of links 71 is manufactured in two parts as shown in FIG. 12. This enables the individual components of each link to be separated so that in assembly, the ribbon stack 80 is inserted within the space between guides 76 and 77 of each link of the segment and when positioned satisfactorily, the "upper" part of each link is then applied in mating relationship with its neighbour. The two halves of each link are secured together to encase the ribbon stack between each pair of guides 76 and 77 respectively. This design provides for a considerable amount of lumen space between the ribbon guides 76 and 77 to permit, in addition, the supply of services such as electricity or compressed air through the lumen space without significant interruption by the control ribbons.

Where a control function needs to be exerted on a particular link, the outer ribbon may be bent back about the outer guide 77 as shown in FIG. 11 and the extremity 82 may be secured to the outer surface 83 of outer guide 77 either by pins or screws or by use of a suitable adhesive.

It will be appreciated by the person skilled in the art that there are fewer design features in each link and since any tension in each ribbon is spread over a considerable surface area of the guide members 76, 77, the frictional loading is much reduced in each case. This allows for improved lubrication, significant frictional reduction and the corresponding reduction of wear over a period of time. In a variant of the embodiment described above, the pivots 90 between each link may be offset or skewed one with respect to another by perhaps as much as a degree or two thus providing a twisting or spiralling effect to the arm. The ribbons are able to accept this slight shift in the pit axis and the device is able to follow a spiral path to correspond with a desired path within the given environment of use for the device.

Referring now to FIGS. 4a–4c and 5, the three dimensional segment differs from the two described above with regard to FIG. 5 in that each of the connecting elements 21 is generally spherical and permits movement of a link over a limited arc in any direction relative to the adjacent link. FIG. 4a shows the segment from a side view perspective while FIG. 4b is a plan view perspective. In this case the links themselves need to be generally spherical and profiled in section as before with the slopping faces 34. In this case, however, at least three wire receiving apertures 51 are provided to permit control of the segments in all three dimensions—as illustrated in FIG. 4c.

A central through passage 32 provided through the elements 21 and the links 20 serve to provide a passageway for control or power supply means to a work head 15.

Figure 6B:
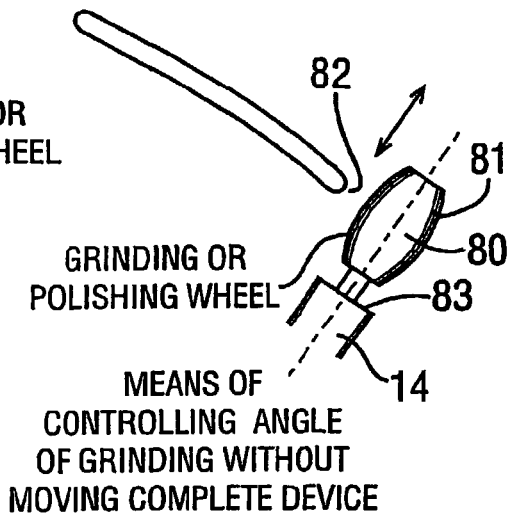

Referring now to FIGS. 6a and 6b, the work head may be provided at the distal end of usually a three-dimensional segment 14 as shown in FIG. 1. To allow for varying angular profiling, for example, provision may be provided for a shaped work head 80 having a profiled work surface 81 (see FIGS. 6a and 6b showing concave and convex work surfaces respectively). Thus, a differing angle of work may be applied at the work site 82 by moving the work head 80 longitudinally with respect to the distal end 83 of segment 14.

Figure 7A:
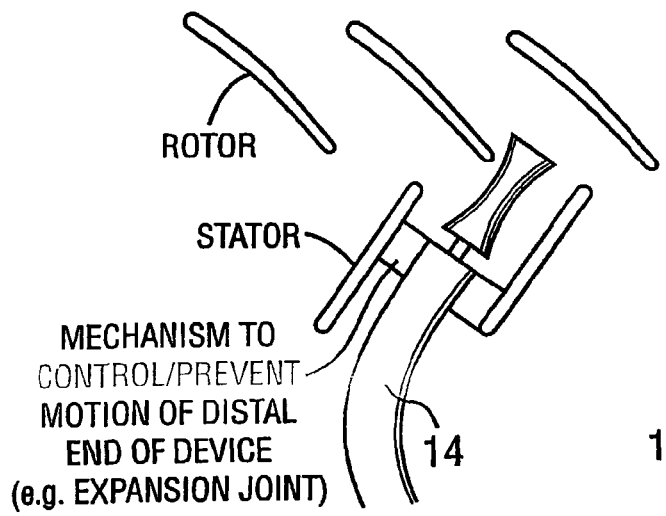
FIG. 7a is a diagrammatic representation of distal end clamping means to locate the work head relative to the work site.
Figure 7B:
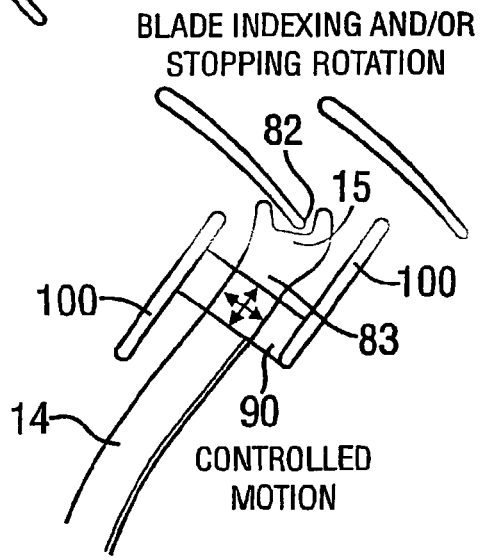

Referring now to FIGS. 7a and 7b, in a particular embodiment of the present invention the segment 14 may be provided at its extremity with an expandable element 90. When following its serpentine path into an engine, the expanded portion 90 is collapsed and forms part of the distal segment 14. When entered between a pair of turbine blades 100 for example, and positioned along the length of each thereof at the appropriate position, the expanded portion 90 may be actuated to expand against the blades 100 to clamp the distal end 83 of segment 14 relative thereto to enable the work piece 15 to operate on an appropriate portion of the work site 82 (see FIG. 7b).

Such an arrangement together with the ability to move the work head 15 longitudinally and laterally with respect to expanding portion 90 enables a limited amount of blade indexing and/or stripping rotation to take place at the distal end of the arm.

Figure 13:
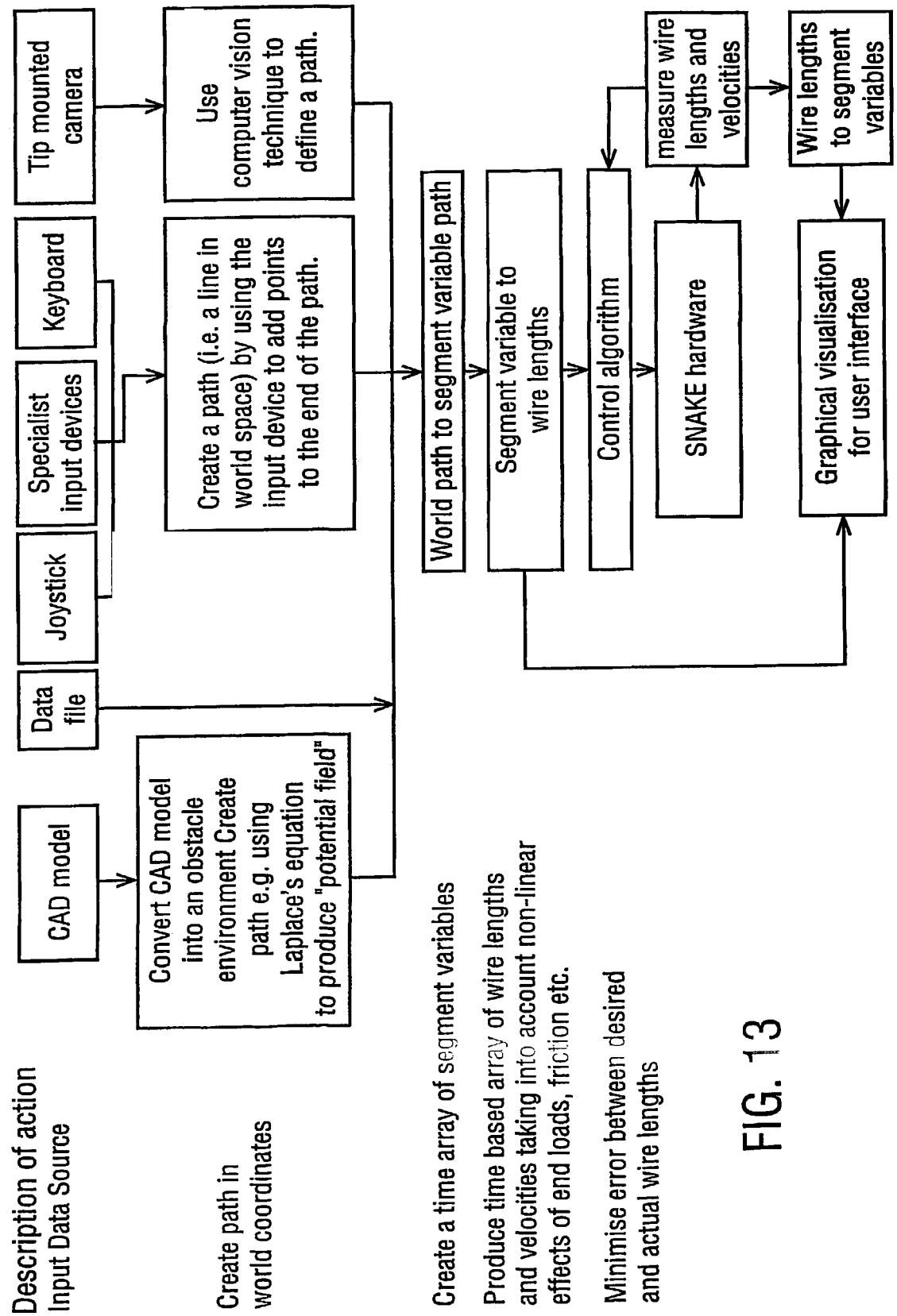
FIG. 13 is flow sheet for the operation of an arm in accordance with the present invention.

A flow sheet giving a description of the action of a typical arm in accordance with the present invention is set out in some detail in FIG. 13 of the drawings accompanying this specification. It will be appreciated by the person skilled in the art that the detail of each step in the flow sheet will be dependent upon the nature of the tasks that the arm is required to perform.

From the foregoing, therefore, it will be seen that the arm, the control mechanism and algorithm in accordance with the present invention permits an arm in accordance with the present invention to extend into an engine or like machine without the need for intermediate guide means. The distal end and work head 15 can be entered into an engine orifice and the various segments of each link can be controlled so that the device can find its way around various obstacles within the engine leading with the work head 15. The extent to which the device can enter the internals of the engine is almost unlimited depending, of course, upon the extent of the arm and the level of control over the individual segments or groups of segments within each link. The motors for each link may be carried on the links themselves or may be provided remotely as described above. The need to fix guide means to guide endoscopic components within the engine is much reduced although the use of guides can be provided to assist in achieving a further reach into the internals of the machine being examined.

It will also be appreciated that with turbines in particular it will be possible to enter the machine via the normal air flows/steam passages within the turbine and that, certainly for examination purposes, separate access ports within the engine will not be a necessity. This has the advantage that it retains the strength and integrity of the engine casing so that in the event of the engine failure at high speed components within the engine can still be contained as part of the containment strategy within the design of the engine without a possible weakening thereof by the inclusion of access ports around the periphery of the engine.

The apparatus in accordance with the present invention and as described above can also be used in conjunction with systematic engine monitoring systems. Proposals have been put forward for the routine monitoring of engine exhausts particularly of gas turbine engines by sensing the ionic component in exhaust gases. By maintaining a record of the ionic emissions of the engine during service it is possible to build up a picture of the where the wear and/or problems within the engine are likely to occur. Combining this information with an algorithm for access to various parts of the engine would enable, in the event of an unacceptable series of measurements of ionic components from engine exhaust monitoring, substantially automated inspection of likely areas of wear.

Such activities would cut and indeed almost eliminate servicing down-time on engines and would ultimately lead to much greater efficiency of operation of such engines and machines and gas turbine engines in particular.

The invention claimed is:

1. A robot arm apparatus comprising:
   a plurality of longitudinal segments arranged sequentially along the arm, each segment movable with respect to the others to define a serpentine path or shape, in which;
   each segment comprises a plurality of links arranged sequentially by articulations between the links, each link movable in at least two dimensions with respect to adjacent links;
   a work head carrier located at a distal end of said arm adapted to carry a tool;
   a controller for controlling at least some of said segments to facilitate control of the shape of the associated segment such that differing segments constituting the arm may assume different shapes where the arm may advance longitudinally along a selected access path to present said tool at a location;

wherein the spatial positioning of each segment is controlled with the arm following a path to guide a work tool into a desired work position;

wherein articulation between individual links in a segment are subjected to a resistance to improve the load capacity and positional determinancy of each link in the segment;

wherein the resistance to articulation is furnished by at least one spring; and wherein the at least one spring is provided such that a compressive force on the spring is less than the total control wire tension, and is selected to give one of a specific bending and a specific rocking stiffness to each joint.

2. The apparatus according to claim 1 wherein each segment is separately controlled.

3. The apparatus according to claim 2 wherein the controller includes a computer for control of the segments, articulations between the links, and spatial disposition.

4. The apparatus according to claim 2 wherein said separate control comprises a servo motor for each segment.

5. The apparatus according to claim 4 wherein the servo motor is mounted within each segment.

6. The apparatus according to claim 4 wherein the servo motor for each segment is remotely located from each corresponding segment.

7. The apparatus according to claim 4 wherein the servo motors are selected from the group consisting of: hydraulic or pneumatic motors.

8. The apparatus according to claim 1 wherein the segments are controlled and driven by wires.

9. The apparatus according to claim 8 wherein at least two wires are provided for each link and wherein adjusting one wire with respect to another controls the attitude of one link with respect to an adjacent link to cause the segment to deform.

10. The apparatus according to claim 1 wherein the controller incorporates a datum for a particular workpiece and includes an algorithm to enable presentation of the tool to a particular position or location relative to that datum.

11. The apparatus according to claim 1 wherein the links within a single segment are articulated in a single plane to facilitate movement of the segment in two dimensions.

12. The apparatus according to claim 1 wherein the links within a single segment are articulated to facilitate movement in three dimensions.

13. The apparatus according to claim 12 wherein the articulation comprises a roller joint.

14. The apparatus according to claim 13 wherein the articulation means is a ball joint.

15. The apparatus according to claim 1 wherein the articulation of the links in a segment is maintained under load by at least one wire under tension.

16. The apparatus according to claim 15 wherein the load applied by the at least one wire under tension maintains stiffness of the joint such that the segment adopts a substantially rigid deformed configuration such that a working force may be applied by tool at the distill end of the arm.

17. The apparatus according to claim 1 wherein the controller includes a driver operating through a length of the arm.

18. The apparatus according to claim 1 wherein at least one segment comprises a plurality of links facilitating bending of the segment in two dimensions only and wherein the movement of the links within the segment is controlled by one of flat ribbons and flat strips of material.

19. The apparatus according to claim 18 wherein said one of flat ribbons and flat strips are of spring steel strip having a thickness of typically one of 25 micron and 50 microns.

20. The apparatus according to claim 1 wherein a rotational joint is provided between pairs of segments such that a portion of the arm is oriented and bends in a plane different from the remaining portion of the arm.

21. The apparatus according to claim 1 wherein at least some of the link and segment articulations are offset from a center line of at least one of the segments and is inclined with respect to an adjacent segment to facilitate spiral articulation of the arm.

22. The apparatus according to claim 1 wherein the controller comprises a redundant robot controller.

23. The apparatus according to claim 1 wherein an algorithm for said controller comprises at least one of trajectory planning techniques and a potential field algorithm based on an adaptation of a Laplace equation.

24. The apparatus as claimed in claim 1 wherein a workhead for the arm includes a clamp for securing the workhead to surrounding structure within the work environment to steady and locate the workhead relative to a work piece.

25. A robot arm apparatus comprising:

a plurality of longitudinal segments arranged sequentially along the arm, each of which segments being movable with respect to each other to define at least one of a serpentine path and a serpentine shape, in which each segment comprises a plurality of links arranged sequentially by articulations between the links, each link being movable in at least two dimensions with respect to adjacent links, wherein all of the plurality of links that comprise each longitudinal segment are substantially identical to one another;

a work head carrier disposed at a distal end of said arm and adapted to carry a tool which is one of a work tool, an examination tool and, combination thereof;

a controller for at least some of said segments to facilitate control of the shape of the associated segment such that different segments constituting the arm assume different shapes wherein the arm may advance longitudinally along an access path to present the tool at a location;

wherein the spatial positioning of each segment can be controlled to enable the arm to follow a path to guide a mounted tool into a desired work position.

26. A robot arm apparatus comprising:

a plurality of longitudinal segments arranged sequentially along the arm, each segment movable with respect to the others to define a serpentine path or shape, in which;

each segment comprises a plurality of links arranged sequentially by articulations between the links, each link movable in at least two dimensions with respect to adjacent links, wherein each of the plurality of links comprise a longitudinal axis, and wherein the longitudinal axes of all of the plurality of links comprising each longitudinal segment are coaxial when each segment is in a rest position;

a work head carrier located at a distal end of said arm adapted to carry a tool;

a controller for controlling at least some of said segments to facilitate control of the shape of the associated segment such that differing segments constituting the arm may assume different shapes where the arm may advance longitudinally along a selected access path to present said tool at a location; and wherein the spatial positioning of each segment is controlled with the arm following a path to guide a work tool into a desired work position.

27. A robot arm apparatus comprising:

a plurality of longitudinal segments arranged sequentially along the arm, each segment movable with respect to the others to define a serpentine path or shape, in which;

each segment comprises a plurality of links arranged sequentially by articulations between the links, each link movable in at least two dimensions with respect to adjacent links, wherein all of the plurality of links comprising each longitudinal segment are moved simultaneously and to the same extent in each direction with respect to each other when each segment is moved;

a work head carrier located at a distal end of said arm adapted to carry a tool;

a controller for controlling at least some of said segments to facilitate control of the shape of the associated segment such that differing segments constituting the arm may assume different shapes where the arm may advance longitudinally along a selected access path to present said tool at a location; and wherein the spatial positioning of each segment is controlled with the arm following a path to guide a work tool into a desired work position.

\* \* \* \* \*